(12) United States Patent
Schneider et al.

(10) Patent No.: US 10,209,105 B2
(45) Date of Patent: Feb. 19, 2019

(54) RETRACTABLE ASSEMBLY

(71) Applicant: Endress+Hauser Conducta GmbH+Co. KG, Gerlingen (DE)

(72) Inventors: Felix Schneider, Dresden (DE); Thomas Pfauch, Leipzig (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 44 days.

(21) Appl. No.: 15/447,348

(22) Filed: Mar. 2, 2017

(65) Prior Publication Data
US 2017/0268910 A1    Sep. 21, 2017

(30) Foreign Application Priority Data

Mar. 16, 2016    (DE) .......................... 10 2016 104 921

(51) Int. Cl.
*G01D 11/24*    (2006.01)

(52) U.S. Cl.
CPC .................................. *G01D 11/245* (2013.01)

(58) Field of Classification Search
None
See application file for complete search history.

(56) References Cited

U.S. PATENT DOCUMENTS

| 3,955,796 | A |   | 5/1976 | Grove |
| 5,085,241 | A | * | 2/1992 | Mieth ............... F16K 1/446 137/1 |
| 6,293,300 | B1 | * | 9/2001 | Dumke ............... F16K 1/446 137/312 |

FOREIGN PATENT DOCUMENTS

| DE | 3801569 A1 | 8/1989 |
| DE | 102011080579 A1 | 2/2013 |
| DE | 102013111057 A1 | 4/2015 |

OTHER PUBLICATIONS

Search Report for German Patent Application No. 10 2016 104 921.2, German Patent Office, dated Mar. 3, 2016, 8 pp.

* cited by examiner

*Primary Examiner* — Paul West
*Assistant Examiner* — Mark A Shabman
(74) *Attorney, Agent, or Firm* — Kelly J. Smith; PatServe

(57) ABSTRACT

The present disclosure relates to a retractable assembly for immersion, flow and attachment measuring systems in analytical process technology that includes an essentially hollow cylindrically shaped housing having a service chamber formed in its interior, where the housing includes an encircling groove open to its interior, where the groove includes an expansion space expanding the groove, where the expansion space is arranged on the side of the groove facing away from the interior, and where the housing includes a leakage path, which connects the expansion space with the environment.

8 Claims, 4 Drawing Sheets

RETRACTABLE ASSEMBLY

CROSS-REFERENCE TO RELATED APPLICATION

The present application is related to and claims the priority benefit of German Patent Application No. 10 2016 104 921.2, filed on Mar. 16, 2016, the entire contents of which are incorporated herein by reference.

TECHNICAL FIELD

The present disclosure relates to a retractable assembly for immersion, flow and attachment measuring systems in analytical process technology for measuring at least one measured variable of a medium in a containment.

BACKGROUND

Retractable assemblies are sold by the group of firms, Endress+Hauser, in great variety, for example, under the designation "Cleanfit H CPA875."

Retractable assemblies are used widely in analytical measurements technology and process automation. They serve to withdraw and reintroduce probes out of and into a process, and thus a medium, without process interruption. The probes are secured in an immersion tube and moved by means of a drive manually or automatically, for example, pneumatically, axially between a process position (measuring) and a service position (maintenance, calibration, washing, probe exchange, etc.). These procedures run within a certain timing cycle or as a function of other determinable or measured parameters.

Probes in the sense of this present disclosure include probes with at least one accommodation for at least one sensor for measuring one or more physical or chemical, process variables.

The scope of use of retractable assemblies for measuring physical or chemical, process variables of a medium, e.g. a fluid, especially a liquid, in process technology is broad. Used for determining the process variables are sensors, such as pH-sensors, conductivity sensors, optical or electrochemical sensors for determining a concentration of a substance contained in the medium to be monitored, e.g. $O_2$, $CO_2$, certain ion types, organic compounds, or the like.

If retractable assemblies are used for accommodating the sensor for determining at least one process variable, the sensor can be checked, calibrated, cleaned and/or replaced in the service position, wherein the sensor is located, in such case, in the housing interior of the retractable assembly, in the so-called service chamber. In order that the medium not be contaminated by the calibration, rinse or cleaning liquid, in the service position, the service chamber is so sealed from the containment, in which the medium is located, that no exchange of medium/liquid can take place. Usually for this purpose, there is located on the media end of the housing of the retractable assembly a seal, which in interaction with the end region of the immersion tube prevents an exchange of medium/liquid. A seat for the seal is located in the immersion tube or in the housing (i.e., service chamber). Used as seal is frequently an O-ring or a shaped seal. The groove for the seal is, in such case, rectangularly shaped in cross section. In such case, gaps frequently arise when the seal is in place.

The gaps and edges form dead spaces, where particles can deposit and scale and/or biofilms can form. These are undesirable, since they degrade the functional ability of the retractable assembly. In the worst case, germs and the like can collect, multiply and so contaminate the medium and make it unusable.

DE 10 2013 111 057 A1 discloses a sealing system and a retractable assembly, which satisfy hygienic requirements. Different hygiene regulations require different types of assembly construction.

SUMMARY

An object of the present disclosure is to provide a hygienic assembly, which satisfies varied regulations.

The object is achieved by a retractable assembly, comprising an: an essentially hollow cylindrically shaped housing having a service chamber formed in its interior, wherein the housing includes an encircling groove open to its interior, wherein the groove includes at least one, preferably two, expansion spaces, expanding the groove, wherein the expansion space is arranged on the side of the groove facing away from the interior; an immersion tube having an end region, wherein the immersion tube is movable axially in the housing between a service position withdrawn from the medium and a process position run into the medium, wherein in the service position the immersion tube is positioned in the service chamber; and at least one seal, wherein in the service position the seal externally closes and gap-freely seals off the service chamber in that an external end region of the immersion tube lies against the seal. In the retractable assembly, the housing includes a leakage path, which connects the expansion space, especially the expansion spaces, with the environment.

A lack of sealing, which leads to contamination of a lower expansion space, cannot be detected. The expansion space can only be cleaned appropriately by disassembly. In regular operation, dirt and microorganisms remain therein, and this represents a danger for the process. The leakage path provides a means by which such contamination can be detected.

The terminology "environment" as used in the present disclosure means the "ambient air," thus the atmosphere around the retractable assembly.

In an embodiment, the housing is embodied as at least two parts. In a first embodiment, the housing includes a medium-near process connection part and a medium-far second part, wherein the groove is formed by corresponding cavities in the process connection part and in the second part. In general, the groove is formed by corresponding cavities in the housing. The two-part construction facilitates the manufacturing, and the installation of the seal is simpler. Other embodiments provide three or more parts of the housing. In this way, the housing can be constructed modularly.

In an embodiment of the leakage paths, these are embodied, for example vertically, by drilling or milling. This is easily done and effectively connects the expansion space with the environment.

In a further embodiment of the leakage paths, these are so embodied that the housing, for instance the process connection, includes at least one annular insert. This represents another way of providing a path from the expansion space to the environment.

Advantageously, the housing includes in the process connection part or in the second part or in the insert an axial hole into the expansion space, in order at least partially to form the leakage path. This hole is easy to manufacture, for instance, by machine processing, such as drilling or milling, and achieves the desired goal, namely the providing of the path from the expansion space to the surrounding air.

In certain embodiments, at least the contacting parts of the process connection and of the insert are of a metal. Mutually contacting metal parts do not, as a rule, seal, so that the desired leakage path results.

In order to detect possible contamination, a measuring device for detection of medium, liquids and the like is connectable to the leakage path.

BRIEF DESCRIPTION OF THE DRAWINGS

The present disclosure will now be explained in greater detail based on the appended drawing, the figures of which show as follows.

Figure 1:
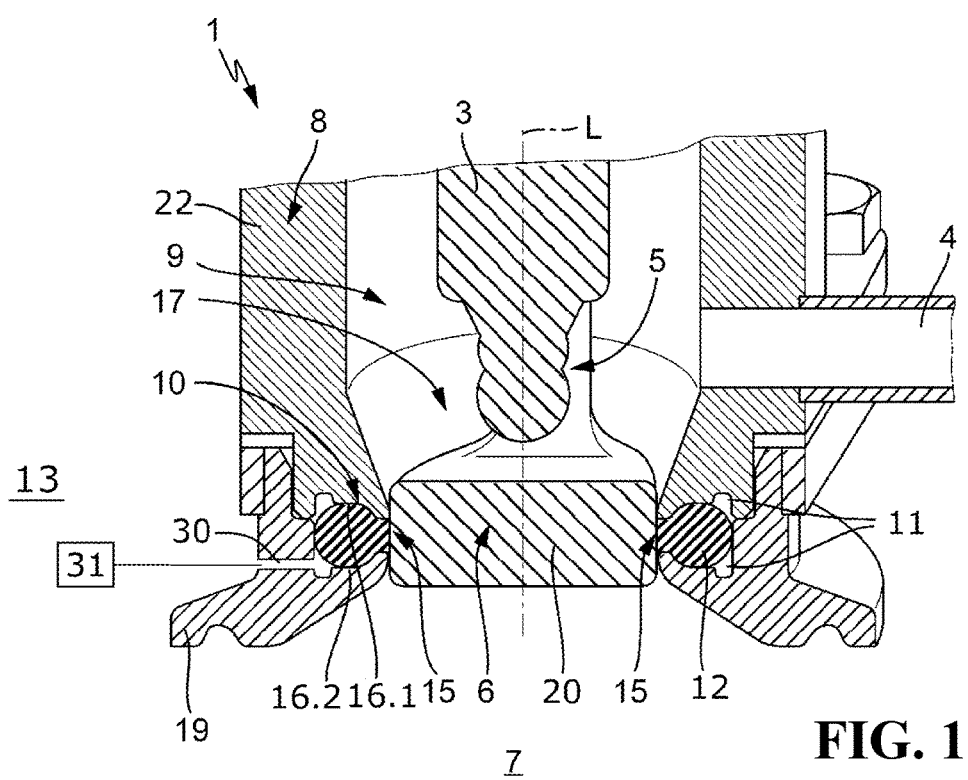
FIG. 1 shows a retractable assembly of the present disclosure in a first embodiment.

In the figures, equal parts are provided with equal reference characters.

DETAILED DESCRIPTION

The retractable assembly of the present disclosure bears the reference character 1 and is shown in FIG. 1. Retractable assembly 1 is composed of an essentially cylindrical housing 8, which can be connected by means of a process connection 19 to a containment (not shown). Process connection 19 can be embodied, for instance, as a flange connection, e.g. of stainless steel. Further details concerning the process connection 19 will be explored below. Located in the containment is the medium 7 to be measured. The containment can be, for instance, a container, vat, tube, pipeline or the like.

The terms "above", "over" and related terms in the sense of this present disclosure mean facing away from the medium 7. The terms "below", "under" and related terms in the sense of this present disclosure mean facing the medium. The terms "outside", "external" and related terms in the sense of this present disclosure mean away from the longitudinal axis L of the housing 8. The terms "inner", "within" and related terms in the sense of this present disclosure mean toward the longitudinal axis L.

FIG. 1 shows the retractable assembly 1 in a service position, which will be further explained in greater detail.

Guided within the housing 8 is an immersion tube 5. A probe is connected with the immersion tube 5 by a holding means (not shown), for example, by a screwed connection, i.e. the probe is mounted in the immersion tube 5. The probe in the sense of this present disclosure includes probes having at least one receptacle for at least one sensor 3 for measuring one or more physical or chemical, process variables, for example, pH-value, also via an ISFET, redox-potential, absorption of electromagnetic waves in the medium, for example, waves with wavelengths in the UV-, IR-, and/or visible region, oxygen level, conductivity, turbidity, concentration of metal and/or non-metal substances or temperature.

When the immersion tube 5 is located in the service position, a portion of the immersion tube 5, especially the sensor 3, is located in the interior 9, in the so-called service chamber 17, for rinsing, cleaning, calibrating, etc. Located at the lower end region 6 (thus toward the medium) of the immersion tube 5 is a closure element 20 for sealing from the process. Closure element 20 seals the interior 9 from the process, and therewith from the medium 7. The medium 7 can be hot, poisonous, corrosive or in other manner damaging for humans and the environment. It is, consequently, necessary that the closure element 20 safely and durably seals. For such purpose, a seal 12 is provided on or in the housing 8, for example a seal in the form of one or more molded sealing units. This will be explained in greater detail below.

In the service position, the various service tasks, such as cleaning or calibration, can be performed. Cleaning, rinsing and calibration liquids can be fed into the interior 9 via a connection 4. The liquid can be drained via a corresponding outlet (not shown in FIG. 1). In an embodiment, there is an upper connection (see, for instance, FIG. 4), wherein the retractable assembly 1 is installed inclined relative to the vertical. The rinse, wash and calibration flow direction can also be reversed.

Immersion tube 5 can be produced of different materials. The state of the art includes immersion tubes 5 of stainless steel, titanium and other chemically resistant materials. Immersion tube 5 can also be produced of a synthetic material such as polyetheretherketone (PEEK), polytetrafluoroethylene (PTFE), a perfluoroalkoxy-polymer (PFA), other synthetic materials or resistant metals, such as, for instance, Hastelloy. The same holds for housing 8.

Immersion tube 5 is mounted such that it can be moved axially in the direction of the central axis L toward or away from the medium 7. Immersion tube 5 is, in such case, run between the service position in the housing 8 (such as described, see FIG. 1) and a process position out of the housing 8, such that the sensor 3 is in contact with the medium 7 in the process position.

The shifting of the immersion tube 5 is by way of a manual or automatic drive, for instance, effected by means of a supply energy (not shown). When energy is supplied through a connection (not shown), the immersion tube 5 moves from the service position into the process position. A further connection (likewise not shown) then serves as a drain. If energy is supplied in the reverse direction, the immersion tube 5 moves from the process position into the service position. Pneumatic, hydraulic and electrical drives are known from the state of the art.

In the process position, the measuring takes place. Via a cage-like opening in the immersion tube 5, the probe, including the sensor 3, has access to the medium 7 to be measured. Alternatively or supplementally, the immersion tube 5 tapers upwardly (thus away from the medium), in order to enable rinsing, cleaning and sterilizing of the immersion tube 5, especially of the closure element 20.

In the following, the seal 12 for sealing the interior 9 from the containment, including from the medium 7, will now be described in greater detail.

Seal 12 lies in a groove 10 made for it in the housing 8. Access to the service chamber 17 is blocked by means of the seal 12 and the closure element 20 in the end region 6 of the immersion tube 5, thus the movable part of the retractable assembly 1.

Housing 8 is formed by a process connection part 19 and a second part 22. Groove 10 is formed by corresponding cavities in the process connection 19 and in the second part 22 of the housing 8. Groove 10 defines a plane, wherein the normal to the plane extends essentially parallel to the longitudinal axis of the housing 8. Joining (for instance, by screwed connection) of the process connection part 19 with the second part 22 creates the groove 10 extending around the housing 8 and open to the interior 9. The shaped seal 12 can be replaced by disassembling process connection part 19 and second part 22 of the housing 8. The two-part construction of the housing 8 facilitates the manufacturing, and installation of the shaped seal 12 is simplified. Also, the groove 10 can then be produced with the required accuracy, especially surface roughness.

Seal 12 includes a first section facing the interior 9 and a second section facing away from the interior 9. In the example, the first section is embodied rectangularly in cross section and the second section circularly in cross section. The first section and the second section form a step where they meet. Various forms, such as, for instance, a wedge shape, embody other options.

Groove 10 and seal 12 are so embodied that a dynamic sealing surface 15 is formed. The dynamic sealing surface 15 is an internally situated, encircling area of the seal 12. The dynamic sealing surface 15 is essentially flush with an inner edge of the housing 8. In an embodiment, the sealing surface 15 is so embodied that a ledge results, whereby a large and therewith cleanable gap of, for example, 1 mm arises.

Interior 9 is gap-freely sealed from the containment, including from the medium 7, especially by the dynamic sealing surface 15 interacting with the immersion tube 5, more specifically the closure element 20. Thus, no gap can form between housing 8 and shaped seal 12. In an embodiment, the dynamic sealing surface 15 protrudes into the interior 9; this region is then in the case of movement of the immersion tube 5 over the shaped seal 12 pressed slightly outwardly.

Additionally, groove 10 is so embodied that at least a first static sealing surface 16.1 and a second static sealing surface 16.2 are formed in the second section. The first static sealing surface 16.1 is arranged on the top of the shaped seal 12 in the second section, while the second static sealing surface 16.2 is arranged on the bottom of the shaped seal 12 in the second section. The first and second static sealing surfaces 16.1, 16.2 seal the interior 9 gap-freely from the external space. Additionally, the first and second static sealing surfaces 16.1, 16.2 assure that the process connection 19 and the second part 22 of the housing 8 are sealed relative to one another. In order further to guarantee that there are no gaps, the cross section of the groove 10 is embodied smaller than the cross section of the shaped seal 12.

The shaped seal 12 is composed, for example, of ethylene-propylene-rubber (EPM), ethylene-propylene-diene-rubber (EPDM), a fluorine containing rubber (FKM), perfluoro rubber (FFKM), polytetrafluoroethylene (PTFE) or a silicone.

Located at the outer part of the groove 10 is an expansion space 11 expanding the groove 10. In at least on embodiment, as shown in the example, there are two expansion spaces 11. The volume of the expansion spaces 11 amounts approximately to 5-20% of the volume of the seal 12. The region of the seal 12 lying opposite the dynamic sealing surface 15 adjoins the expansion spaces 11.

In the case of temperature change, for example, because of a sterilization procedure, the seal 12 can expand into the expansion spaces 11 without reducing the assurance of absence of gaps at the dynamic, first and second static sealing surfaces 15, 16.1, 16.2. In other words, no gap forms at any temperatures. Depending on the material of the shaped seal 12, temperature changes from −20° C. to +140° C. are possible.

To meet hygienic requirements, it may be necessary to clean, i.e. to rinse, wash, and, when required, to sterilize the seal 12. Immersion tube 5 moves into a position, which is located between the service position and the process position. This is locked by a locking apparatus. The locking apparatus is, for instance, a locking element, self-limiting drive or automatically operating mechanism.

Rinse, cleaning or sterilization medium inflowing through the lower connection 4 flows around the seal 12 and, thus, rinses, cleans or sterilizes it. The inflowing medium can drain into the medium 7 (which, when required, is turned off), respectively into the containment.

In a first embodiment of the retractable assembly of the invention 1, such includes a leakage path 30, which is embodied as a vertical bore or milled passageway. This is shown as a connection of the lower expansion space 11 to the environment 13, thus to the ambient air. Equally possible is a connection to the upper expansion space or to both expansion spaces. Connected to the leakage path 30 is a measuring device 31 for detection of medium 7, liquids, etc. Alternatively, a regular visual checking by the user can occur. Thus, it can be detected, when some type of medium is located in the expansion space 11.

Figure 2:
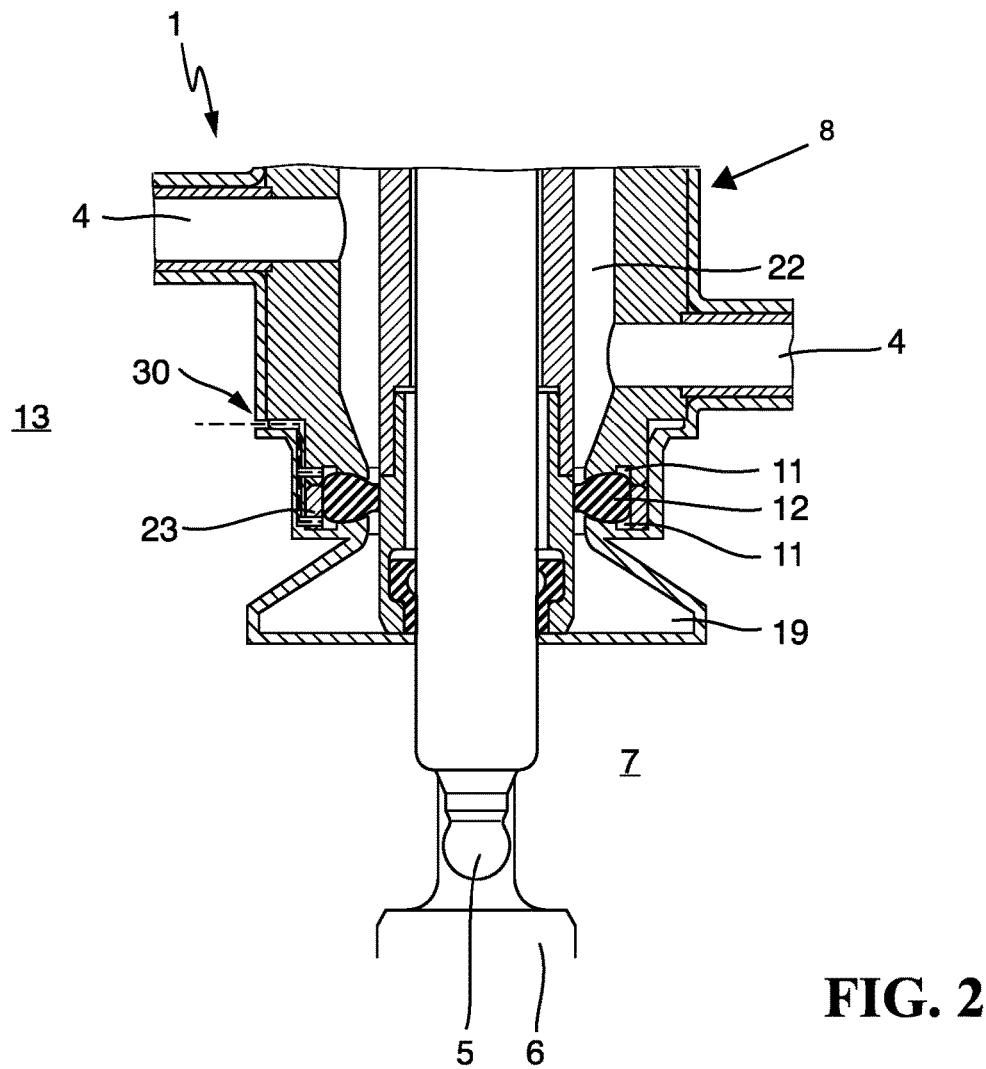
FIG. 2 shows a retractable assembly of the present disclosure in a second embodiment.

A second embodiment is shown in FIG. 2. In FIG. 2, the retractable assembly is in the process position. As has been mentioned, housing 8 is composed of a process connection part 19 and a second part 22. In contrast to the form of embodiment in FIG. 1, the process connection part 19 has been modified; see FIG. 3A in this regard. In this case, an annular insert 23 is inserted; see FIG. 3B. Insert 23 serves as part of the seal geometry. In case the expansion spaces 11, especially the lower space, are/is contaminated with some type of medium, this medium can flow at the contact surface between insert 23 and process connection 19 outwardly via the leakage path 30 and be detected, for instance, by means of a corresponding detection unit 31 (not shown in FIG. 2).

At least the contacting parts of the process connection 19 and the insert 23 are metal. The metal contact area between insert 23 and process connection 19 is, thus, embodied as a leakage path 30.

Figure 3A:
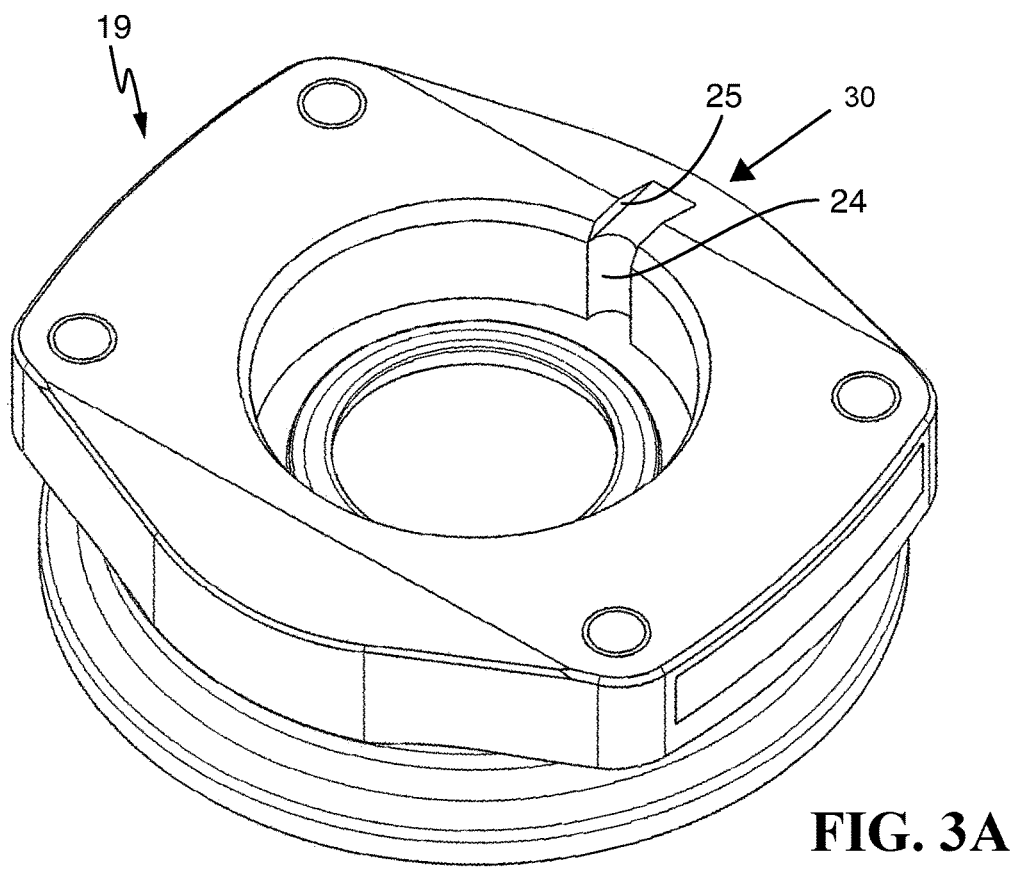
FIGS. 3A and 3B show a process connection and an insert of the retractable assembly of FIG. 2.
Figure 3B:
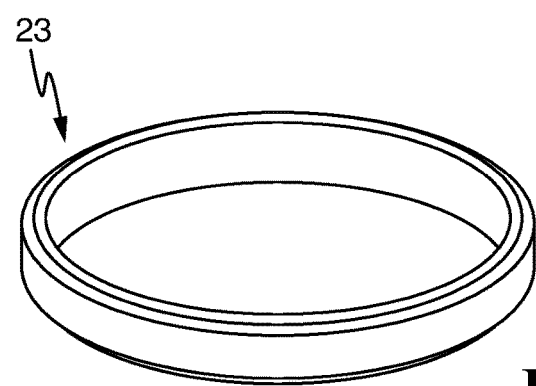

As shown in FIG. 3A, housing 8, here process connection 19 (or in certain embodiments the second part 22), includes an axial blind hole 24 to the expansion space 11 and forms together with a vertical section 25 at least partially the leakage path 30. In an additional alternative, the insert 23 includes the leakage path 30, more exactly the blind hole 24.

Figure 4:
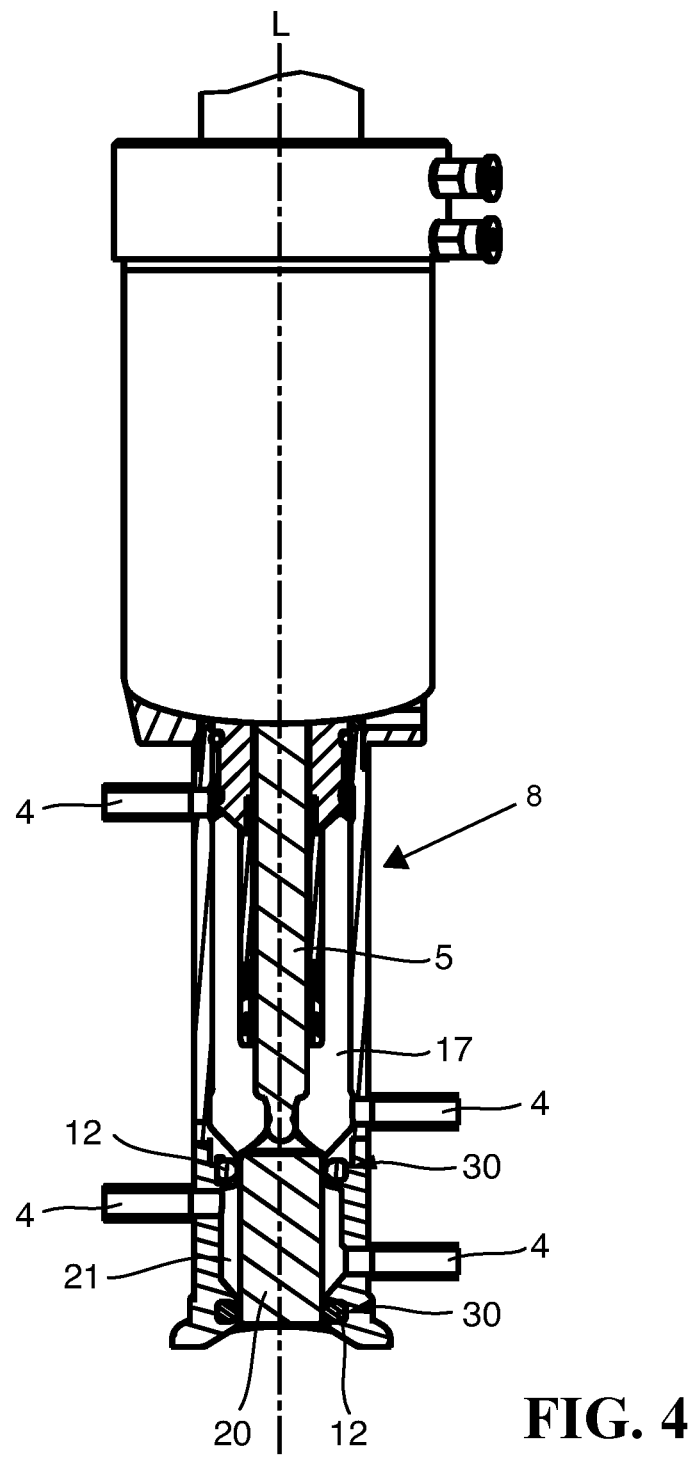
FIG. 4 shows a retractable assembly of the present disclosure with a rinse chamber.

In an embodiment, as shown in FIG. 4, there is located in the housing 8 below the service chamber 17, thus between the service chamber 17 and the containment, another chamber, a rinsing chamber 21. Especially in the case of hygienic applications, rinsing chamber 21 can be utilized as an additional barrier between the medium 7 and the service chamber 17, so that in the case of a replacement of the sensor 3, a double sealing of the containment is assured, as required for certain permits (e.g., EHEDG EL Aseptic Class I). Counting the service chamber 17, then two different chambers are available for performing work on the probe. An example of such work is sterilization or calibration of the probe in the service chamber 17. A plurality of rinse/wash connections 4 can be present. Service chamber 17 and rinsing chamber 21 are likewise sealed from one another by seal 12. Corresponding leakage paths 30 are shown. These can be implemented as above described as vertical bores or by means of inserts.

The invention claimed is:

1. A retractable assembly for immersion, flow and attachment measuring systems in analytical process technology for measuring at least one measured variable of a medium in a containment, comprising:

a hollow, cylindrically shaped housing having a longitudinal axis and having an interior with a service chamber formed therein, the housing including an encircling groove open to its interior, wherein the groove includes a designated seal expansion space expanding the groove, the designated seal expansion space disposed on a side of the groove facing away from the interior;

an immersion tube having an end region, wherein the immersion tube is movable axially in the housing between a service position withdrawn from the medium and a process position in which the immersion tube extends into the medium, wherein in the service position the immersion tube is positioned in the service chamber;

a seal positioned in the groove, wherein in the service position the seal externally closes and gap-freely seals off the service chamber from the environment at the seal and an external end region of the immersion tube in that the external end region lies against the seal;

wherein a portion of the seal expands into the designated seal expansion space when exposed to a temperature change;

wherein the housing includes a leakage path connecting the designated seal expansion space with the environment; and a device for detection a liquid or a medium in the leakage path.

2. The retractable assembly of claim 1, wherein the leakage path is embodied as a bore or a milled passageway.

3. The retractable assembly of claim 1, wherein the leakage path is embodied as a bore or a milled passageway, wherein the bore or milled passageway extends substantially in the direction of the longitudinal axis.

4. The retractable assembly of claim 1, wherein the housing is formed of a process connection part adjacent the medium and a second part adjacent the process connection part and opposite the medium, wherein the groove is formed by corresponding cavities in the process connection part and in the second part.

5. The retractable assembly of claim 4, wherein the process connection includes an annular insert.

6. The retractable assembly of claim 5, wherein the housing includes, in the process connection part, the second part or the insert, an axial hole into the designated seal expansion space, at least partially forming the leakage path.

7. The retractable assembly of claim 5, wherein the process connection and the insert have contacting parts and at least the contacting parts of the process connection and the insert are metal.

8. The retractable assembly of claim 1, wherein the immersion tube houses a probe and a sensor.

* * * * *